United States Patent
Hajianpour (10) Patent No.: US 8,123,747 B2
(45) Date of Patent: *Feb. 28, 2012

(54) APPARATUS FOR EXTERNAL FIXATION OF A FRACTURED DISTAL RADIUS WITH ANGULARLY ADJUSTABLE PIN CLAMPING MEANS

(75) Inventor: Mohammed Ali Hajianpour, Fort Lauderdale, FL (US)

(73) Assignee: Nutek Orthopaedics, Inc., Fort Lauderdale, FL (US)

( * ) Notice: Subject to any disclaimer, the term of this patent is extended or adjusted under 35 U.S.C. 154(b) by 377 days.

This patent is subject to a terminal disclaimer.

(21) Appl. No.: 12/460,680

(22) Filed: Jul. 23, 2009

(65) Prior Publication Data
US 2010/0076436 A1     Mar. 25, 2010

Related U.S. Application Data

(63) Continuation-in-part of application No. 11/893,592, filed on Aug. 16, 2007, now Pat. No. 7,717,916.

(51) Int. Cl.
*A61F 5/04* (2006.01)
(52) U.S. Cl. ............................................. 606/54; 606/57
(58) Field of Classification Search ............... 606/53–59, 606/280, 70, 71, 282, 105, 90
See application file for complete search history.

(56) References Cited

U.S. PATENT DOCUMENTS

| | | | |
|---|---|---|---|
| 1,997,466 A * | 4/1935 | Longfellow | 606/59 |
| 4,554,915 A | 11/1985 | Brumfield | |
| 4,620,533 A * | 11/1986 | Mears | 606/54 |
| 4,628,922 A * | 12/1986 | Dewar | 606/56 |
| 5,304,177 A * | 4/1994 | Pennig | 606/58 |
| RE34,985 E | 6/1995 | Pennig | |
| 5,443,464 A * | 8/1995 | Russell et al. | 606/54 |
| 5,545,162 A | 8/1996 | Huebner | |
| 5,591,169 A * | 1/1997 | Benoist | 606/59 |
| 5,779,703 A | 7/1998 | Benoist | |
| 5,797,908 A * | 8/1998 | Meyers et al. | 606/54 |
| 6,197,027 B1 | 3/2001 | Hajianpour | |
| 6,585,736 B2 | 7/2003 | Hajianpour | |
| 7,147,639 B2 | 12/2006 | Berki et al. | |
| 7,153,302 B1 | 12/2006 | Hajianpour | |
| 2003/0055425 A1* | 3/2003 | Hajianpour | 606/57 |
| 2003/0153910 A1* | 8/2003 | Janowski et al. | 606/56 |
| 2003/0225407 A1* | 12/2003 | Estrada, Jr. | 606/54 |
| 2006/0229605 A1* | 10/2006 | Olsen | 606/54 |

FOREIGN PATENT DOCUMENTS
WO     WO 91/00111     8/1991

* cited by examiner

*Primary Examiner* — Eduardo C Robert
*Assistant Examiner* — Lynnsy Schneider
(74) *Attorney, Agent, or Firm* — Ronald V. Davidge (57) ABSTRACT

An external fixation device for holding bone fragments in place includes a housing having a number of rotationally adjustable pin holders, each of which is held by a clamping member that simultaneously clamps the pin holder within an internal mounting surface of the housing and a bone pin within the pin holder. A first embodiment includes a number of internal mounting surfaces, each of which can include a single pin holder. A second embodiment includes one or two internal mounting surfaces, each of which holds a row of pin holders that is clamped in place by a single clamping member. Other embodiments include such pin holders arranged with elements including an array of pin holding positions for fixing fragments at a fractured end of a bone, such as a fractured distal radius.

13 Claims, 7 Drawing Sheets

APPARATUS FOR EXTERNAL FIXATION OF A FRACTURED DISTAL RADIUS WITH ANGULARLY ADJUSTABLE PIN CLAMPING MEANS

CROSS-REFERENCE TO A RELATED APPLICATION

This is a continuation-in-part of a U.S. patent application Ser. No. 11/893,592, filed Aug. 16, 2007 now U.S. Pat. No. 7,717,916.

BACKGROUND OF THE INVENTION

1. Field of the Invention

This invention relates to apparatus for the external fixation of fractured bones, and, more particularly, to such apparatus having means for adjustably mounting and clamping a number of bone pins to a housing.

2. Summary of the Background Art

External fixation often provides the best method for holding bone fragments in place during he healing of a severe bone fracture, in which multiple bone fragments are formed. In the external fixation process, bone pins or wires ate surgically attached to the individual bone fragments and to intact sections of bone, so that a desired alignment of multiple fragments can be maintained during the healing process. The individual bone pins or wires are also attached to a frame that is external to the body to be held in a fixed configuration. Then, after the bone fragments have joined to one another in a satisfactory manner, the bone pins or wires are removed from the bones and from the body in another surgical procedure. With external fixation, an ability to hold individual bone fragments in place often makes in possible to achieve results that cannot be achieved using other conventional techniques, such as casting.

Since serious bone fractures can occur in many different ways in various parts of the body, forming various configuration of bone fragments, it is highly desirable that a device for external fixation should be configured in a variety of different ways, reducing the number of different types of fixation devices that need to be held in inventory to meet expected demands. To this end, the patent literature includes a number of descriptions of fixation devices that can be assembled from multiple elements in various ways or that can be adjusted to provide various configurational features.

One method to obtain this kind of flexibility has been to provide a plate having a number of holes defining locations in which bone pins or wires may be clamped, with only a variable subset of the holes being used in the treatment of a typical fracture. For example, U.S. Pat. No. 7,153,303 describes a fixture including several holes for clamping members to hold bone pins disposed within an elongated portion and a number of holes in a rectangular pattern, which can accommodate a variety of pin configurations. Such an arrangement is used, for example, to fasten the elongated portion of the fixture to the shaft of the radius bone within the arm and to attach various fragments within a broken wrist to a pattern of pins clamped within the rectangular array. A configuration for applying external fixation to a fractured tibia is also described as including a frame an elongated lower section for fastening the frame to the shaft of the tibia using bone pins extending along a straight line and an arcuate section extending from each side of the upper end of the elongated lower section for clamping bone pins extending into bone fragments within the upper portion of the tibia. U.S. Pat. No. 5,779,703 describes a bone organizer having a number of holes through which wires are attached to bone fragments.

Another method for obtaining flexibility within an external fixation device is to provide a number of clamping elements holding one or more bone pins, with the clamping elements being attached to one another by devices providing for pivotal adjustment. For example, U.S. Pat. No. 5,624,440 describes a fixture including a number of clamping elements, each of which clamps a pair of bone pins extending parallel to one another and a rod to which the clamping elements are attached by means of a pair of pivoting clamps providing for rotational adjustment and clamping about two axes perpendicular to one another. U.S. Pat. No. RE34,985 describes a fixation device having a pair of elongated carriers, each of which supports a pair of bone screws that are movable along the carrier by rotating a spindle. The carriers are joined to one another by a connector including a rigid rod and a ball at each end. The balls are received by partly spherical sockets that can be fixed relative to the balls through screws. U.S. Pat. No. 4,554,915 describes an external fixation frame including a fixation block from which one or more arms extend, with a ball and socket joint connecting each arm to the block for universal movement thereabout. Setscrews are provided for tightening the ball and socket joints. International Pat. Appl. Pub. No. WO 91/111 describes a fixation device having a pair of clamping members, each of which includes a row of holes into which bone pins may be inserted and clamped, with the clamping members being connected by a tube, into which a rod extends from one of the clamping members, while a ball from the other connecting member extends into a partially spherical hole within the tube. Setscrews are provided for clamping the rod and ball in place within the tube.

What is needed is a bone fixation device having the flexibility of adjusting the angle at which individual bone pins extend from a housing or frame, preferably with such an adjustment being provided through a clamping device that simultaneously clamps both the linear extension of the bone pin, along its length, and its angle relative to the housing or frame.

The fracture of the distal radius is one of the most common human fractures, occurring in as many as 350,000 people per year in the United States alone. The conventional processes both for reducing such a fracture and for maintaining the bones in proper alignment during the subsequent healing process involves applying and maintaining an extension force across the fracture, with ligamental taxis being relied upon to hold the bones in place. The process for treating a fractured distal radius is described in the 1901 edition of *Gray's Anatomy* in the following manner, "The treatment consists of flexing the forearm, and making a powerful extension from the wrist and elbow, depressing at the same time the radial side of the hand, and retaining the parts in that position by well padded pistol shaped splints."

A common method for the treatment of a fractured distal radius involves the use of standard immobilizing cast techniques, preventing movement of the radiocarpal joint throughout the course of rehabilitation. A problem with this method is that it sometimes results in inadequate internal fixation, which can cause deformity, pain, and prolonged disability.

The process of external pin fixation is often used in the repair of a fractured distal radius. This process initially involves the surgical insertion of skeletal traction pins on both sides of the fracture, with a frame being connected to the pins for immobilizing the bones, and for holding them together until the fracture is mended. Conventional methods for applying external pin fixation for the treatment of a fractured distal radius provide for the immobilization of the radiocarpal joint, so that the hand cannot be flexed.

Examples of frames used in this way are found in U.S. Pat. Nos. 4,554,915 and 5,545,162. Each of these frames rigidly but adjustably connects a pair of pins extending into the metacarpal bones with a pair of pins extending into the radius on the proximal side of the fracture. While this type of fixation often provides an improvement over conventional casting techniques in the management of severe fractures of the distal radius, immobilization of the radiocarpal joint during the treatment period typically results in a long period of stiffness and disability after the external fixation device is removed. Typically the external fixation device is left in place during the healing process for six to eight weeks. After the fixation device is removed, three to six months are required for the patient to regain motion of his hand. Thus, what is needed is a fixation device providing adequate fixation during the healing process while allowing flexure in the radiocarpal joint of a fractured distal radius may alternately be repaired using a permanently installed fixation plate with screws and blades extending into the radius and into the broken fragments. The fracture of the distal radius is one of the most common major fractures, occurring in as many as 350,000 people per year in the United States alone. The conventional processes both for reducing such a fracture and for maintaining the bones in proper alignment during the subsequent healing process involves applying and maintaining an extension force across the fracture, with ligamental taxis being relied upon to hold the bones in place. The process for treating a fractured distal radius is described in the 1901 edition of *Gray's Anatomy* in the following manner, "The treatment consists of flexing the forearm, and making a powerful extension from the wrist and elbow, depressing at the same time the radial side of the hand, and retaining the parts in that position by well padded pistol-shaped splints."

One method for the treatment of a fractured distal radius involves the use of standard immobilizing cast techniques, preventing movement of the radiocarpal joint throughout the course of rehabilitation. A problem with this method is that it sometimes results in inadequate internal fixation, which can cause deformity, pain, and prolonged disability.

The process of external pin fixation is often used in the repair of a fractured distal radius. This process initially involves the surgical insertion of skeletal traction pins on both sides of the fracture, with a frame being connected to the pins for immobilizing the bones, and for holding them together until the fracture is mended. Conventional methods for applying external pin fixation for the treatment of a fractured distal radius provide for the immobilization of the radiocarpal joint, so that the hand cannot be flexed. Examples of frames used in this way are found in U.S. Pat. Nos. 4,554,915 and 5,545,162. Each of these frames rigidly but adjustably connects a pair of pins extending into the metacarpal bones with a pair of pins extending into the radius on the proximal side of the fracture. While this type of fixation often provides an improvement over conventional casting techniques in the management of severe fractures of the distal radius, immobilization of the radiocarpal joint during the treatment period typically results in a long period of stiffness and disability after the external fixation device is removed. Typically the external fixation device is left in place during the healing process for six to eight weeks. After the fixation device is removed, three to six months are required for the patient to regain motion of his hand. Thus, what is needed is a fixation device providing adequate fixation during the healing process while allowing flexure in the radiocarpal joint.

While this type of fixation often provides an improvement over conventional casting techniques in the management of severe fractures of the distal radius, immobilization of the radiocarpal joint during the treatment period typically results in a long period of stiffness and disability after the external fixation device is removed. Typically, the external fixation device is left in place during the healing process for six to eight weeks. After the fixation device is removed, three to six months are required for the patient to regain motion of his hand.

An example of a fixation device providing adequate fixation during the healing process while allowing flexure in the radiocarpal joint is described in U.S. Pat. No. 6,197,027, the disclosure of which is incorporated herein by reference. This fixation device includes a number of pins clamped within pin mounting holes. Each pin extends through a flexible sleeve and through a clamping nut. Each pin-mounting hole includes a pilot hole guiding the pin and an internally threaded portion engaging an externally threaded portion of the clamping nut. As the clamping nut is tightened, the flexible sleeve is longitudinally compressed, so that it expands transversely to clamp itself within the pin-mounting hole and to clamp the pin within itself. The fixation device, which is configured particularly for external fixation of a fractured distal radius, includes a first number of such pins configured for attachment within a shaft portion of the radius and a second number of such pins configured to attachment to one or more fragments of the fractured radius. The fixation device also includes a sliding attachment block supporting a number of pins extending for lateral attachment to such a fragment.

However, in the holes used in the device of U.S. Pat. No. 6,197,027 to mount pins within the first number of pins, what is needed is a somewhat more simple, and therefore cost-effective, method for holding the pins in place. Such a method would preferably eliminate the need for the flexible sleeves to translate longitudinal compression into transverse clamping forces. In the holes used to mount pins within the second number of pins, what is needed is a more simple method, which will preferably clamp all of the pins in use simultaneously. Two or more of these pins may be used to clamp a single bone fragment in two or more places, or several pins may be used to clamp several bone fragments. Furthermore, since the process of setting a distal radius fracture typically includes an application of extension to the distal fragment(s), what is needed is a feature simplifying the application of such extension forces as the fixation device is installed on the fractured radius.

U.S. Pat. No. 5,545,162 describes a bone fixator including a proximal pin mounting block and a distal pin connected by a medial assembly, which connects the pin mounting blocks in a manner which is pivotally adjustable, and which further allows for adjustment of the distance between the pin mounting blocks. However, what is needed is a fixture for facilitating this distance adjustment so that it can be retained and gradually increased, instead of being lost when a clamping screw is loosened to allow movement. Furthermore, the method of U.S. Pat. No. 5,545,162 does not include the installation of pins within the fragments of bone; instead pins from the distal pin mounting block extend into the finger bones, adding a requirement that the extension forces must be directed through the wrist. To provide mobility of the hand and wrist, the fixture is pivoted with a ball joint. What is needed is a fixture rigidly holding pins extending into the bone fragments instead of into the bones of the fingers. Such a fixture would have advantages of holding different configurations of fragments in place, of holding them more rigidly, and of providing greater freedom of wrist movement.

U.S. Pat. No. 6,585,736 describes a fixture configured to provide external fixation of a fractured distal radius by including a first number of bolts for pins extending downward from the fixture into one or more bone fragments and a second number of holes for pins extending downward from the fixture into the shank, of the radius. The fixture also includes a sliding block through which rods extend to hold pins directed laterally into the fragment(s). A sliding plate including a number of holes aligned with the first number of holes is moved by a pair of setscrews to clamp the pins extending through the first number of holes. The second number of holes includes a hole within a sliding structure allowing a single pin to be moved with a fixture to provide extension between the fragments and the shank of the radius. What is needed is a method for adjusting the angular relationships between certain individual pins in such a fixture and a more simple method to hold pins directed laterally into the bone fragment(s).

SUMMARY OF THE INVENTION

In accordance with one aspect of the invention, apparatus is provided for external fixation of a plurality of fragments at an end of a bone, wherein the apparatus comprises a housing, a first plurality of bone pins, a clamping bracket, a second plurality of bone pins, at least one clamping screw, and a third plurality of bone pins. The housing includes an elongated shank mounting portion, a fragment attachment pin array section, and a lateral fragment mounting section. The fragment attachment pin array section is disposed at a first end of the elongated shank mounting portion having a first array of pin mounting holes The lateral fragment mounting section extends parallel to the elongated shank mounting portion and downward from an edge of the fragment attachment pin array section. The lateral fragment mounting section includes a first plurality of apertures and a first plurality of threaded holes, each adjacent an aperture in the first plurality of apertures.

Within a shank mounting portion of the apparatus, the first plurality of bone pins is clamped within the shank mounting portion to extend downward from the shank mounting portion for attachment within a shank portion of the bone.

Within a fragment attachment array section of the apparatus, the clamping bracket includes a clamping plate having a second array of pin mounting holes. The second plurality of bone pins extends through holes within the first array of pin mounting holes and through holes within the second array of pin mounting holes, and extends downward for attachment to fragments within the plurality of fragments. The at least one clamping screw holds the clamping bracket against the housing so that the second array of holes is misaligned with the first array of holes to hold the second plurality of bone pins in place within the first array of holes.

Within a lateral fragment attachment portion off the apparatus, the third plurality of bone pins is clamped within the lateral fragment mounting section to extend laterally for attachment to fragments within the plurality of fragments. The first plurality of pin holders is held within the housing, Each of these pin holders includes a pin mounting hole, a spherically rounded surface engaging an internal mounting surface within the housing, and a deformable portion. The third plurality of bone pins are each held within the pin mounting hole in a pin holder within the first plurality of pin holders to extend through an aperture in the first plurality of apertures. An angle, relative to the housing, at which each of the bone pins extends through the aperture is varied by pivoting the pin holder within the housing. The first plurality of clamping members each includes a threaded surface engaging a threaded hole within the first plurality of threaded holes. As the clamping member is rotated in a first direction, an engagement force between the spherically rounded surface of the pin holder clamped in place within the housing by the clamping member and the internal mounting surface within the housing is increased to hold the pin holder in place within the housing, and deflection of the deformable portion of the pin holder is increased to hold a bone pin in place within the pin mounting hole of the pin holder. As the clamping member is rotated opposite the first direction, the engagement force between the spherically rounded surface of the pin holder and the internal mounting surface within the housing is decreased to allow rotation of the spherically rounded surface of the pin holder within the internal mounting surface of the housing and to allow movement of the bone pin within the pin mounting hole of the pin holder.

Preferably, the pin mounting hole within each of the pin holders extends in a straight line through a center of the spherically rounded surface, and each of the pin holders includes a first slot extending across the pin mounting hole and partially across the pin holder, displaced inward from a first end of the pin mounting hole, forming a first deflectable portion of the pin holder between the first slot and the first end of the pin mounting hole. Preferably, each of the pin holders additionally includes a second slot extending across the pin mounting hole and partially across the pin holder, displaced inward from a second end of the pin mounting hole, forming a second deflectable portion of the pin holder between the second slot and the second end of the pin mounting hole.

The elongated shank mounting portion may include a threaded hole and an aperture adjacent the threaded hole, and wherein the apparatus additionally comprises an additional pin holder holding an angularly adjustable bone pin in the first array of bone pins, and an additional clamping member.

The elongated shank mounting portion may additionally include a pin adjustment slot, with the apparatus additionally comprising a nut and a collet screw. The nut, which is mounted to slide within the pin adjustment slot, includes inclined surfaces engaging the pin adjustment slot to prevent rotation of the nut within the pin adjustment slot and to prevent removal of the nut from the pin adjustment slot. The collet screw also slides within the pin adjustment slot. A linearly adjustable bone pin within the first plurality of bone pins extends through a hole within the collet screw, which includes a deformable threaded portion engaging the nut. As the collet screw is rotated in a first direction, an engagement force between the collet screw and the linearly adjustable bone pin is increased to hold the linearly adjustable bone pin in place collet screw and to hold the nut in place within the pin adjustment slot. As the collet screw is rotated opposite the first direction, the engagement force between the collet screw and the linearly adjustable bone pin is decreased to release the linearly adjustable bone pin to move within the collet screw and the nut is released to slide within the pin adjustment slot. This apparatus may additionally include a distraction clamp removably holding the linearly adjustable bone pin; and a distraction screw engaging the distraction clamp and the housing. Turning the distraction screw in a second direction moves the linearly adjustable bone pin toward a proximal end of the housing, while turning the distraction screw opposite the second direction allows the linearly adjustable bone pin to move away from the proximal end of the housing.

The clamping bracket may additionally include a hole engaging a pin extending from the housing to hold the clamping bracket in place on the housing without a bone pin extending through a hole within the first and second arrays of pin mounting holes. Furthermore, the clamping bracket man additionally include an additional clamping plate having a third array of pin mounting holes, with the second and third arrays of mounting holes being held adjacent opposite sides of the first array off pin mounting holes.

DETAILED DESCRIPTION OF THE INVENTION

Figure 1:
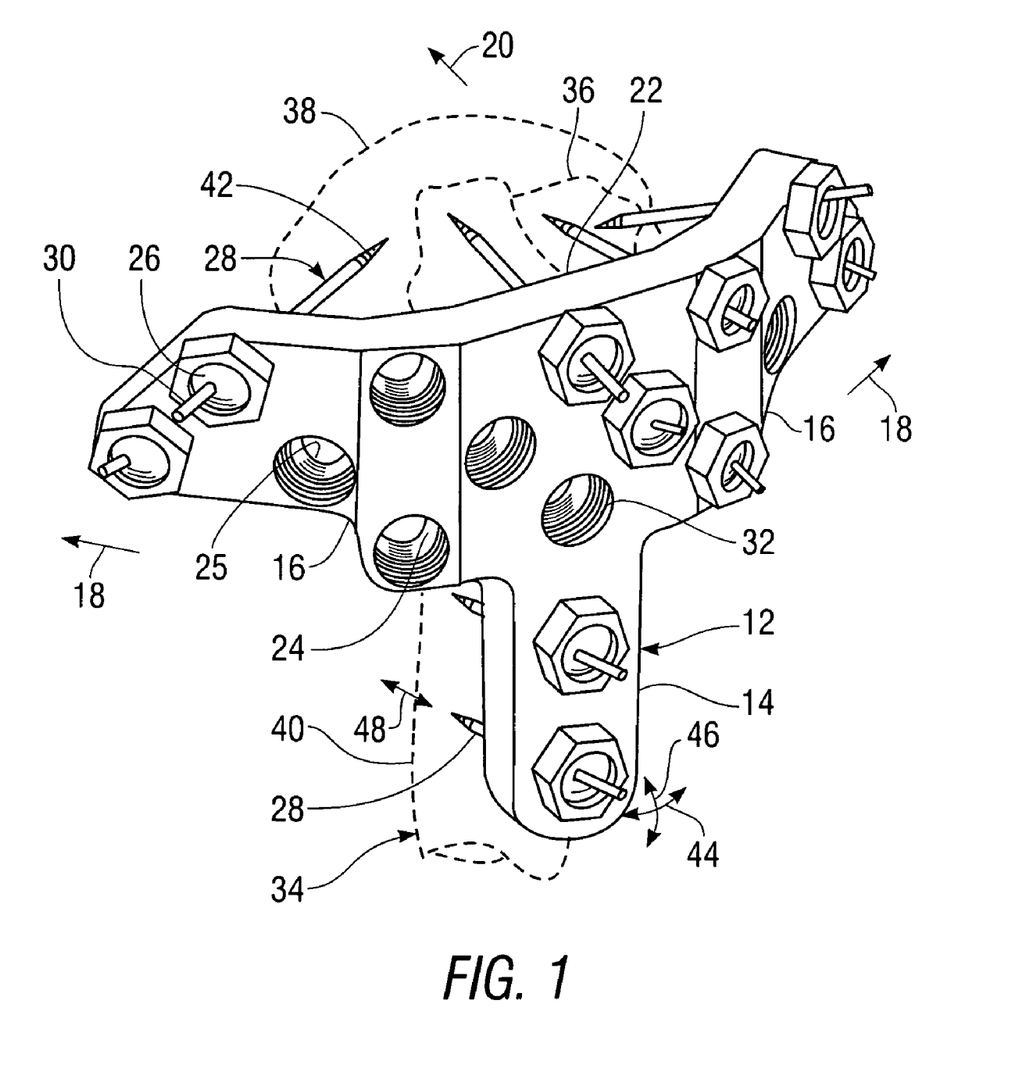
FIG. 1 is a perspective view of a device for external fixation of bone fragments, built in accordance with a first embodiment of the invention and shown as used for a proximal fracture of the humerus.

FIG. 1 is a perspective view of a device 10 for the external fixation of bone fragments, built in accordance with a first embodiment of the invention. The device 10 includes a housing 12 having a vertically elongated central portion 14 and a lateral portion 16 extending outward, in the directions of arrows 18, and rearward, in the direction of arrow 20, from each side of an upper end 22 of vertically elongated central portion 14: The vertically elongated central portion 14 includes a first plurality of the internal mounting surfaces 24; each of which extends outwardly from an aperture 25 within the housing 12, while each lateral portion 16 includes at least one of the internal mounting surfaces 24 extending from an aperture 25. Some of the internal mounting surfaces 24 mount pin holders 28 holding bone pins 28, with the pin holders 28 being held in place by clamping members 30 engaging threaded surfaces 32 of the housing 12. This arrangement provides for the placement of bone pins 28 at various levels extending downward from the upper end 22 of the vertically elongated central portion 14, with the lateral portions 16 being inclined relative to one another so that bone pins 28 can extend inward around a fracture area from these portions 16.

In the example of FIG. 1, the device 10 is shown with various bone pins 28 attached to a fractured humerus bone 34, holding a number of fragments 36 in place at an upper end 38 of the humerus bone 34, with bone pins 28 held within the vertically elongated central portion 14 of the housing 12 attached to the shaft portion 40 of the humerus bone 34. Each of the bone pins 28 includes a threaded end 42 that is driven into engagement with a portion of the bone 34 by a driving tool (not shown) rotating a non-circular surface (not shown) at an end of the bone pin 28 opposite the threaded end 42. After the bone pin 28 is fastened into place, the bone pin 28 is preferably cut off outwardly adjacent the pin holder 26 in which it is held to limit the distance through which the bone pin 28 extends outwardly from the device 10. The configuration of the device 10 is adjustable in several ways, with pin holders 26 being placed in a subset of the internal mounting surfaces 24, so that bone pins 28 are placed at locations appropriate for the external fixation of a particular fractured bone. In addition, the individual pin holders 26 are angularly adjustable so that each bone pin 28 can be adjusted and clamped in place through a vertical angle of adjustment 44 and through a horizontal angle of adjustment 46, with the bone pin 28 additionally being adjustable along its axis in the directions of arrows 48.

Figure 2:
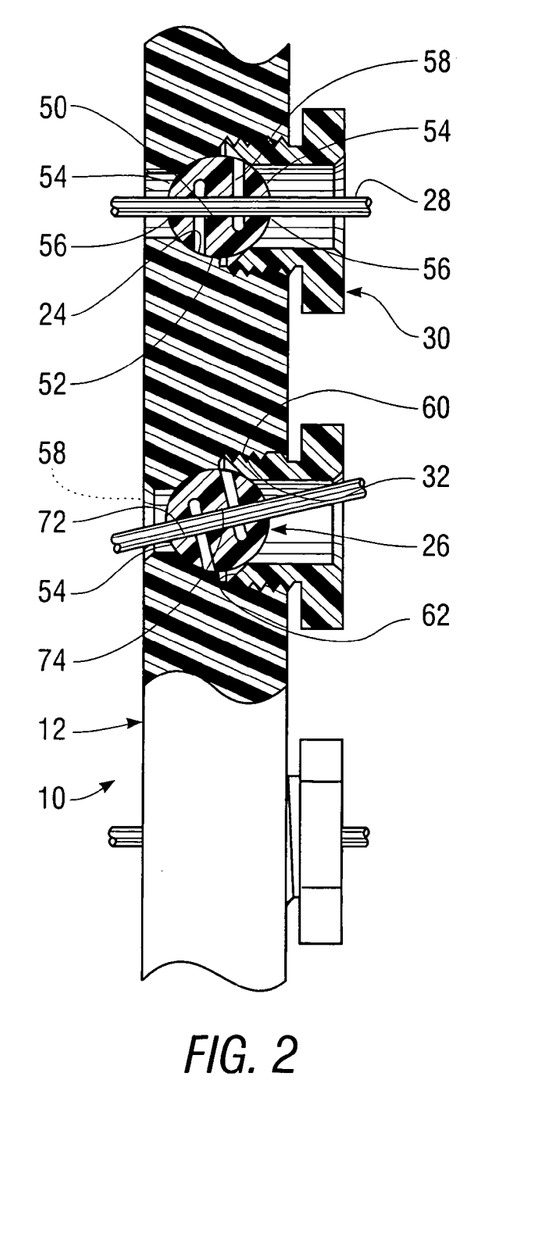
FIG. 2 is a fragmentary and partly cross-sectional lateral elevation of the device of FIG. 1.

FIG. 2 is a fragmentary and partly cross-sectional lateral elevation of the device 10, particularly showing features of the internal mounting surfaces 24 within the housing 12, of the pin holders 26, and of the clamping members 30. Each of the pin holders 26 includes a pin mounting hole 50, a spherically rounded surface 52 engaging an internal mounting surface 24 within the housing, and deformable portions 54 at each end 56 of the pin mounting hole 50. Each of he deformable portions 54 is formed by a slot 58 extending inward in a direction perpendicular to the pin mounting hole 50, extending across the pin mounting hole 50 and part of the way across the pin holder 26. Each of the of clamping members 30 clamps a pin holder 26 in place within the housing 12 and deflects the deformable portions 54 of the pin holder 26 to hold the pin 28 in place within the pin holder 26. Each clamping member 30 includes a threaded surface 60 and an annular surface 62 engaging a deformable portion 54 of a pin holder 26. The threaded surface 60 of each of the clamping members 30 engages one of the threaded surfaces 32 of the housing 12.

Thus, each of the bone pins 28 extends through an aperture 25 within the housing 12 at angles, in horizontal and vertical planes relative to the housing 12, that can be varied by rotation of the spherically rounded surface 52 of the pin holder 26 through which the bone pin 28 extends within the internal mounting surface 24. A bone pin may extend in a direction perpendicular to the aperture 25 or at an angle of inclination relative to such a direction of, for example, up to thirty degrees.

Figure 3:
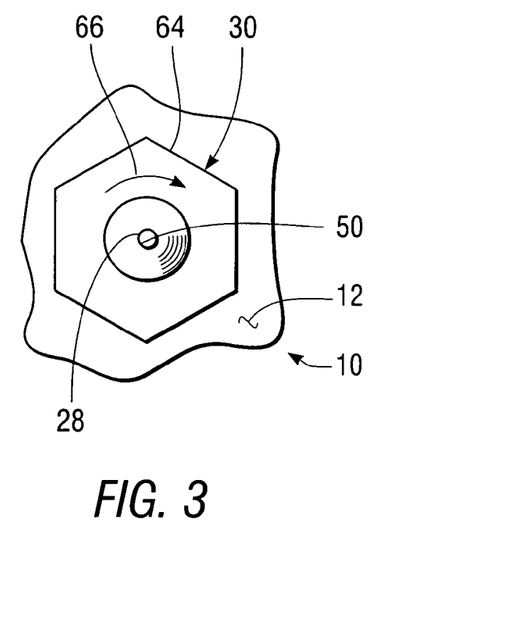
FIG. 3 is a fragmentary front elevation of the device of FIG. 1.

FIG. 3 is a fragmentary front elevation of the device 10, showing one of the clamping members 30, which is provided with a noncircular surface 64 to facilitate rotation of the clamping member 30. As the clamping member 30 is tightened by rotation in a first direction, indicated by arrow 66, an engagement force between the spherically rounded surface 52 of the pin holder 26 clamped in place within the housing 12 by the clamping member 30 and the internal mounting surface 24 within the housing 12 is increased to hold the pin holder 26 in place within the housing 12, and deflection of the deformable portions 54 of the pin holder is increased to hold the bone pin 28 in place within the pin holder 26. As each of the clamping members 30 is rotated opposite the first direction of arrow 66, the engagement force between the spherically rounded surface 52 of the pin holder 26 and the internal mounting surface 24 within the housing 12 is decreased to allow rotation of the spherically rounded surface 52 of the pin holder 26 within the internal mounting surface 24 of the housing 12 and to allow movement of the bone pin 28 within the pin mounting hole 50 of the pin holder 26. For example, the device 10 may be provided with a box wrench (not shown) for loosening and tightening the clamping members 30.

Figure 4:
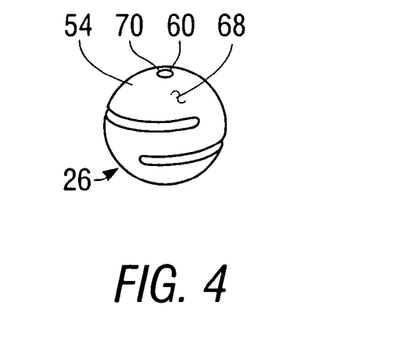
FIG. 4 is a perspective view of a pin holder within the device of FIG. 1.

FIG. 4 is a perspective view of one of one of the pin holders 26, which has a spherical external surface 68. The clamping member 30 includes a pair of slots 58 extending perpendicular to the pin mounting hole 50, inward across the pin mounting hole 50 and partly across the pin holder 26, so that a deformable portion 54 is formed between each end 56 of the pin mounting hole 50 and the slot 58 that is nearer to the end 56.

As shown in FIG. 3, the pin mounting hole 50 extends through a center of the spherical external surface 68, being divided by the slots 58 into a deflectable part 72 within each of the deformable portions 54 and a central part 74 extending between the slots 58. When the clamping member 30 is tightened by rotation in the direction of arrow 66 to increase an engagement force holding the pin holder 26 in place, the deformable portions 54 are deflected inward, bring the deflectable parts 72 of the pin mounting hole 50 out of alignment with the central part 74 thereof, so that the bone pin 28 is clamped in place within the pin mounting hole. Then, when the clamping member is loosened by rotation opposite the opposite the direction of arrow 66 to decrease the engagement force holding the pin holder 20 in place, the deformable portions 54 return outward, so that the deflectable parts 72 of the pin mounting hole 50 return into alignment with the central part 74 thereof, allowing movement of the bone pin 28 within the pin mounting hole 50. For example, the bone pin 28 may be rotated as much as thirty degrees from a central position in which the bone pin 28 extends perpendicularly from the housing 12.

Figure 5:
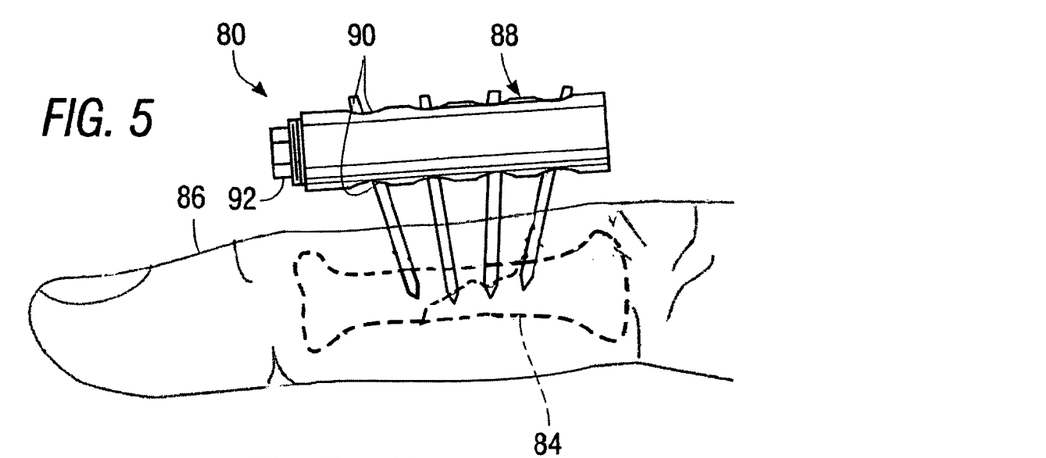
FIG. 5 is a side elevation of a device built in accordance with a first version of a second embodiment of the invention and shown attached to bone fragments within a finger.

FIG. 5 is a side elevation of a device 80 for external fixation of bone fragments, built in accordance with a second embodiment of the invention and shown with pins 82 attached to several fragments of bones 84 within a finger 86. The device 80 includes a housing 88, having a plurality of apertures 90 through which the pins 82 extend, and a first clamping member 92, which is turned to clamp the pins 82 in place within the housing 88.

Figure 6:
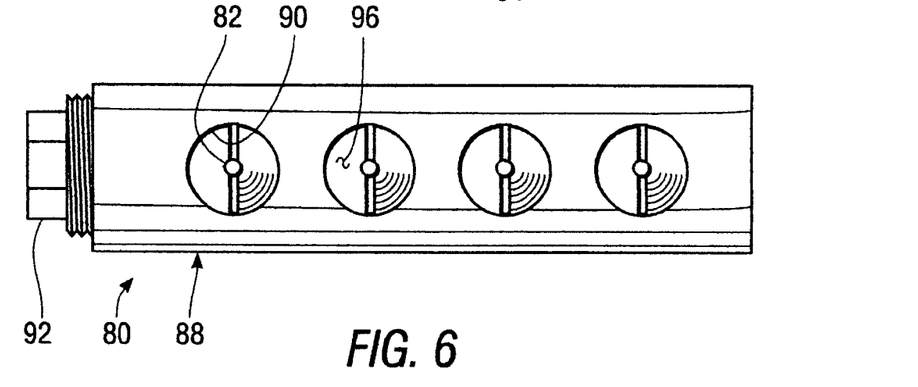
FIG. 6 is a plan view of the device of FIG. 5.
Figure 7:
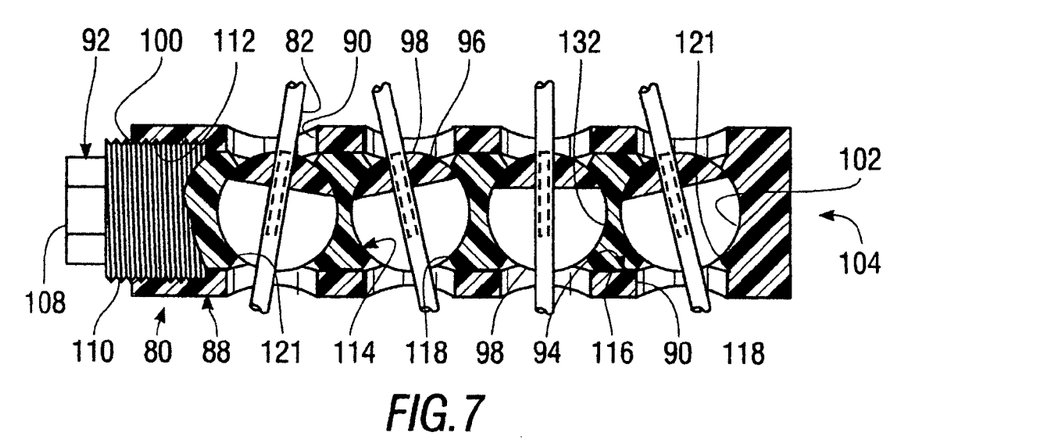
FIG. 7 is a cross-sectional side view of the device of FIG. 5.

Features of the device 80 will now be discussed with reference being made to FIGS. 6 and 7. FIG. 6 is a plan view of the device 80, while FIG. 7 is a cross-sectional side elevation thereof. The housing 88 includes a single internal mounting surface 94, with the single clamping member 92, clamping each of a plurality of pin holders 96 in place within the first internal mounting surface 94 and deflecting a deformable portion 98 of each of the pin holders 96 to hold the bone pin 82 therein in place. For example, the first internal mounting surface 94 is formed as an elongated cylinder having an open end 100 and a closed end 102, with the plurality of pin holders 96 disposed in a first row 104 within the first internal mounting surface 94. The first clamping member 92 is movable within the open end 100 of the elongated cylinder to provide a clamping force acting against the pin holder adjacent the open end 100 of the internal mounting surface 94. For example, the first clamping member is moved in the direction of arrow 106 by turning a non-circular portion 108 of the clamping member with a threaded portion 110 thereof in engagement with a threaded portion 112 of the housing 88. A clamping force, arising from the engagement between the clamping member 92 and the pin holder 96 adjacent the open end 100, is transmitted between the pin holders 96 adjacent one another within the first row 104. For example, the device 80 may be provided with a socket head wrench for loosening and tightening the clamping member 92.

Figure 8:
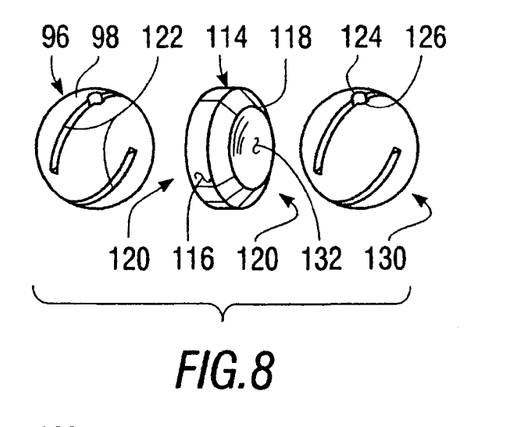
FIG. 8 is an exploded perspective views of adjacent pin holders and a spacer disposed therebetween within the device of FIG. 5

FIG. 8 is an exploded perspective view of two pin holders 96 and a spacer 114 disposed between the pin holders 96. Preferably, the device 80 additionally includes a spacer 114 between each pair of pin holders 96 adjacent one another in the first row 104, with the clamping force being transmitted between the pin holders 96 adjacent one another through the spacer 114. The spacer 114 includes a peripheral surface 116 engaging the first internal mounting surface 94 of the housing 88 between adjacent apertures 90 within the housing 88 and a circular edge 118 engaging the adjacent pin holder 96 at each side 120 of the spacer 114 to hold the pin holder 96 in place within the housing 88. Without the spacers 114, the pin holders 96 would be allowed to move into the adjacent apertures 90, so that the pin holders 96 would not be rigidly mounted within the first mounting surface 94. Preferably, as shown in FIG. 7, the first clamping member 92 and the closed end 102 of the first internal mounting surface 94 additionally also include a circular edge 121 engaging the adjacent pin holder 96 to hold the pin holder 96 in place within the housing 88.

Each of the pin holders 96 additionally includes a slot 122 extending inward from each end 124 of a pin mounting hole 126 to form a part of the deformable portion 98 of the pin holder 96 at each end 124 of the pin mounting hole 128. The slots 122 at each end 124 of the pin mounting hole 128 extend along the pin mounting hole 126, being disposed perpendicular to one another. Preferably, the slots 122 are formed to extend inward, across one another in a central portion 130 of the pin holder 96, so that the central portion 130 can be deflected by contact with a concave surface 132 of the spacer 114, even if one of the slots 122 is positioned to extend between the concave surfaces 132 of spacers 114 at either side of the pin holder 96.

Thus, each of the bone pins 82 extends through an aperture 90 within the housing 88 at angles, in directions perpendicular to one another, that can be varied by rotation of the spherically rounded pin holder 96 through which the bone pin 28 extends within the internal mounting surface 94. A bone pin may extend in a direction perpendicular to the aperture 90 or at an angle of inclination relative to such a direction of, for example, up to thirty degrees.

Figure 9:
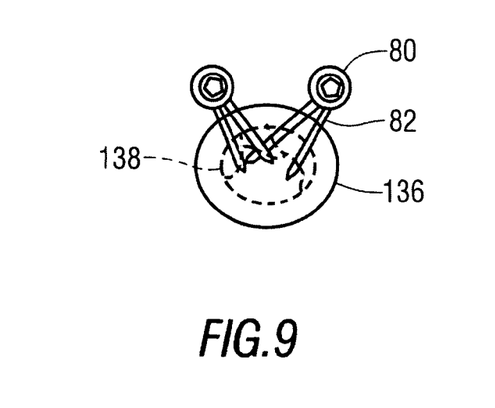
FIG. 9 is a partly sectional end view of a finger having two of the devices of FIG. 5 attached to bone fragments.

FIG. 9 is a partly sectional end view of a finger 136 with two of the devices 80 holding bone pins 82 in engagement with bone fragments 138. Two or more of the devices 80 may be used in this way so that the bone pins 82 can be directed from various locations extending around the bone fragments.

While the pin holders 96, 134 have been described in terms of use with the device 90 of FIGS. 5-7, it is understood that such pin holders 96, 134 can alternately be used with a device otherwise as described above in reference to FIGS. 1-3, with deformable portions 98, 150 being deflected in response to tightening the clamping member 30 to hold pins in place within the pin holders 56, 134.

Figure 10:
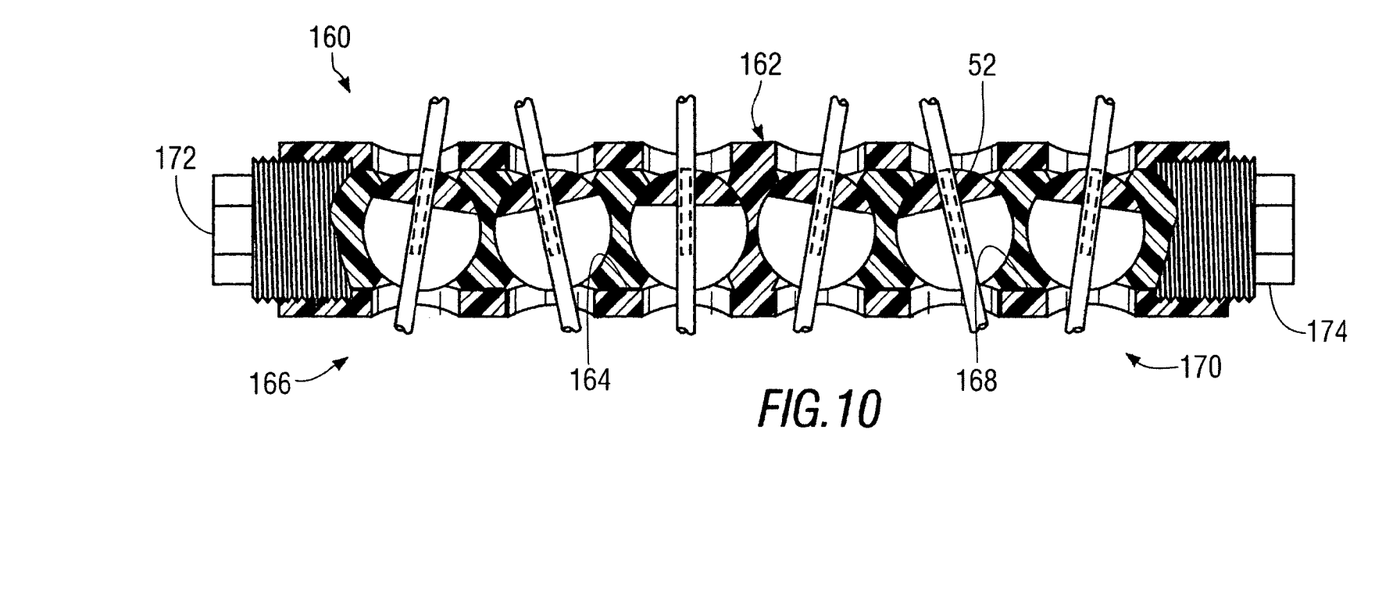
FIG. 10 is a cross-sectional side view of a device built in accordance with a second version of the second embodiment of the invention.

FIG. 10 is a cross-sectional side elevation of a device 160 built in accordance with a second version of the second embodiment of the invention to include a housing 162 having both a first internal mounting surface 164 holding a plurality of pin holders 52 in a first row 166 and a second internal mounting surface 168 holding a plurality of pin holders 52 in a second row 170. The device 160 additionally includes a first clamping device 172, which is turned to clamp and release all of the pin holders 52 in the first row 166, and a second clamping device 174, which is used to clamp and release all of the pin holders 52 in the second row 170. Other features of the device 100 are as described above in reference to FIGS. 5-9 for the device 80 built in accordance with the first version of the second embodiment of the invention. While the example of FIG. 10 shows three pin holders 52 held within each of the internal mounting surfaces 168, it is understood that each of the internal mounting surfaces in general can be configured to hold two or more pin holders 52.

Figure 11:
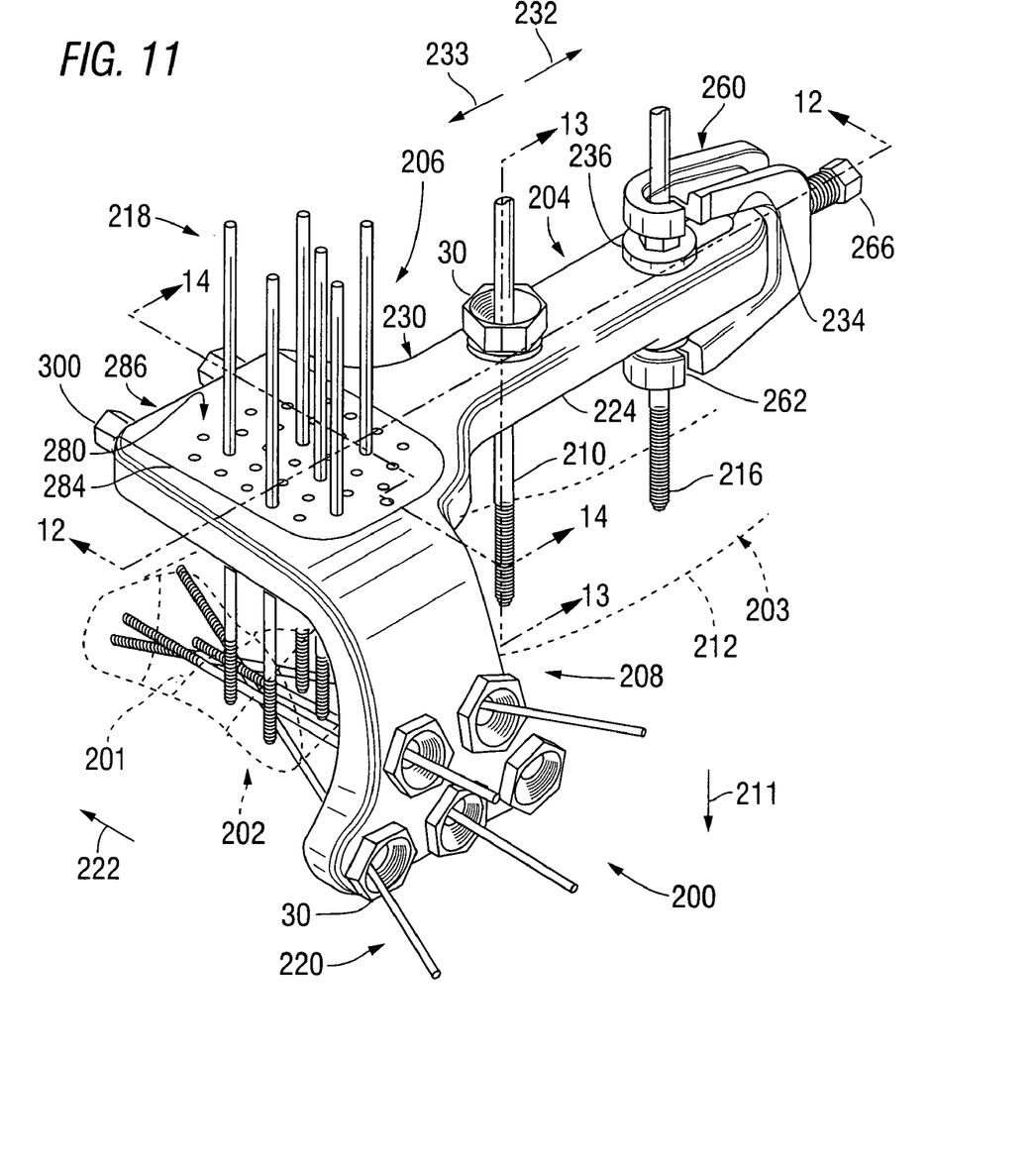
FIG. 11 is a perspective view of a device built in accordance with a third embodiment of the invention for the external fixation of fragments within a fractured distal radius.

FIG. 11 is a perspective view of a device 200 built in accordance with a third embodiment of the invention for the external fixation of fragments 201 within a fractured distal end 202 of a radius 203. The device 200 includes an elongated shank mounting section 204, a fragment attachment pin array section 206, and a lateral fragment mounting section 208. The elongated shank mounting section 204 includes an angularly adjustable shank mounting pin 210 extending downward, in the direction of arrow 211, to be fastened into a shank portion 212 of the distal radius 202 and a linearly adjustable shank mounting pin 216, also extending downward, in the direction of arrow 211, to be fastened into the shank portion 212. The fragment attachment pin array section 206 includes a plurality of attachment pins 218 extending downward, in the direction of arrow 211, to be fastened into a number of the bone fragments 201. The lateral fragment mounting section 208 includes a number of angularly adjustable fragment mounting pins 220 extending laterally, generally in the direction of arrow 222 into a number of the bone fragments 201. (The directions described herein are established according to an assumption that the hand, not shown, but attached to the radius 212, is held outward with the palm facing downward, in the direction of arrow 211.)

Non-bridging fixation is achieved by fastening all of the pins 210, 216, 218, 220 of the device 200 into the fragments 201 and the shank portion 212 of the radius 203. None of these pins 210, 216, 218, 220 are fastened into the carpal bones, not shown, but adjacent to the fragments 201, or the bones of the hand, so that the hand and wrist can be flexed and moved normally, without a loss of mobility during the healing process requiring fixation.

Figure 12:
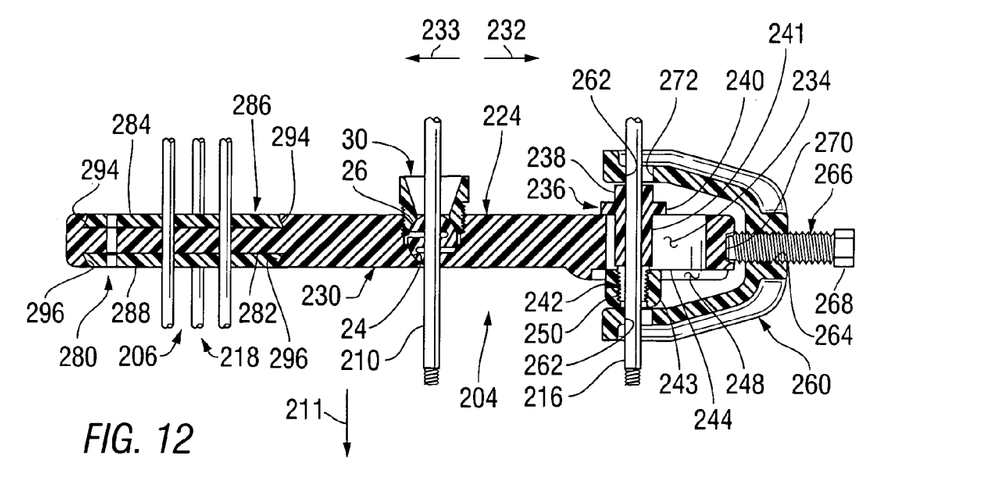
FIG. 12 is a longitudinal cross-sectional view of the device of FIG. 11, taken as indicated by section lines 12-12 therein.

FIG. 12 is a longitudinal cross-sectional view of the device 200, taken as indicated by section lines 12-12 in FIG. 11 to show means for attaching the angularly adjustable shank mounting pin 210 and the linearly adjustable shank mounting pin 216 to a shank mounting section 224 within a housing 230 of the device 200. The angularly adjustable shank mounting pin 210 is rotatably mounted and clamped in place as described above in reference to FIGS. 2-4, with various similar elements being accorded like reference numerals.

Figure 13:
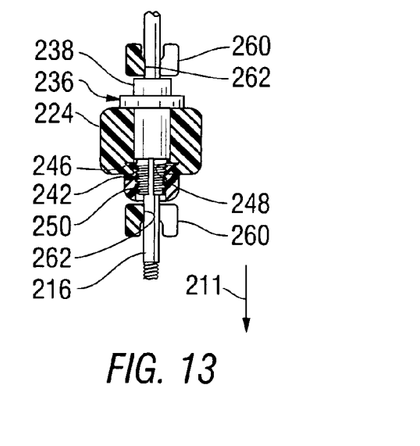
FIG. 13 is a transverse cross-sectional view of the device of FIG. 11, taken as indicated by section lines 13-13 therein.

FIG. 13 is a transverse cross-sectional view of the device 200, taken as indicated be section lines 13-13 in FIG. 11, showing means for attaching the linearly adjustable shank mounting pin 216, the angularly adjustable shank mounting pin 210, and the fragment attachment pins 212. The linearly adjustable shank mounting pin 216 is mounted to slide along the shank mounting housing section 224 in the axial directions of arrows 232, 233, with a collet screw 236 sliding within an adjustment slot 234 in the housing section 224. The collet screw 236 includes a non-circular section 238, a flange 240, a barrel 241 sliding within the slot 234, and a threaded section 242 engaging a nut 243. The nut 243 slides within a slot 244, with dovetail surfaces 246 of the nut 243 engaging dovetail surfaces 248 of the slot 244 to prevent rotation of the nut 243 while allowing the nut 243 to slide within the slot 244. The threaded section 242 of the collet screw 236. includes a plurality of threaded clamping members 250, which move inward to clamp the adjustable shank mounting pin 216 in place within the collet screw 236 as the as the collet screw 236 is rotated into engagement with the nut 243 using the non-cylindrical surface 238 of the collet screw 236.

A distraction clamp 260 is provided to apply a distraction force in the direction of arrow 233 through the fragment mounting pins 218, 220 to the bone fragments 201 within the fractured distal end 202 of the distal radius 202 (shown in FIG. 11). The distraction clamp 260 includes a pair of hooks 262 engaging the linearly adjustable shank mounting pin 216 and a threaded hole 264 engaging a distraction adjustment screw 266. This distraction force is applied, after the surgical placement of the fragment mounting pins 218, 220 within the bone fragments 201 and after the surgical placement of the shank mounting pin 216 within the bone shank portion 212, but before the surgical placement of the adjustable shank mounting pin 210 within the bone shank portion 212, by turning the distraction adjustment screw 266 by means of a non-circular surface 268 to move the housing 230 in the distraction direction of arrow 233. Then, when a suitable level of distraction has been achieved, the linearly adjustable shank mounting pin 216 is clamped into place using the collet screw 236, and the adjustable shank mounting pin 210 is surgically installed within the bone shank portion 212 and clamped to the housing 230 using the clamping member 30. Finally, the distraction clamp 260 is removed from the fixation device 201 by turning the distraction screw 266 so that it is disengaged from the proximal end 270 of the housing 230, and by disengaging the distraction clamp 260 from the linearly adjustable shank mounting pin 216, with the pin 216 passing through slots 272 of the distraction clamp 260.

Figure 14:
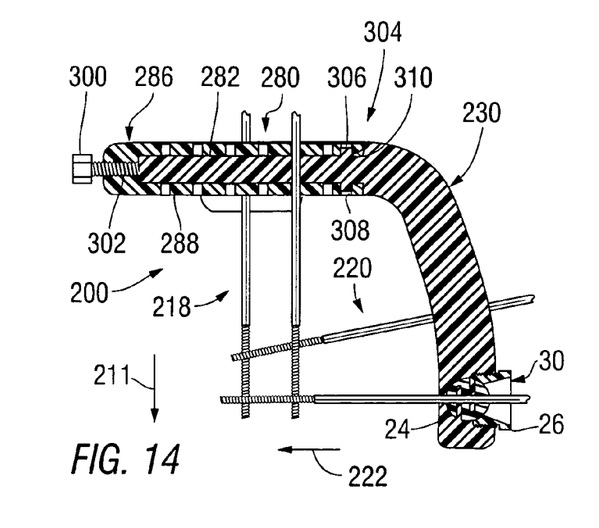
FIG. 14 is a transverse cross-sectional view of the device of FIG. 11, taken as indicated by section lines 14-14 therein.

FIG. 14 is a transverse cross-sectional view of the device 200, taken as indicated by section lines 14-14 in FIG. 11 to show means for mounting and clamping the plurality of fragment attachment pins 218 and the angularly adjustable fragment mounting pins 220. For mounting the fragment attachment pins 218, similar patterns of holes 280 are provided within a distal portion 282 of the housing 230, within a top plate 284 of a U-shaped pin clamping bracket 286, and within a bottom plate 288 of the clamping bracket 286. The U-shaped pin clamping bracket 286 is mounted to slide in and opposite the lateral direction of arrow 222, with inclined sides 294 of the plates 284, 286 within the clamping bracket 286 sliding along inclined sides 296 of the housing 230. The alignment between the patterns of holes 280 within the clamping bracket 286 and the holes 280 within the housing 230 is adjusted using a pair of screws 300, each engaging a threaded hole 302 within the clamping bracket 286 to press an adjacent surface 304 of the housing 230. As the screws 300 are tightened, the holes 280 within the clamping bracket 286 are moved in the direction of arrow 211 relative to the holes 280 within the housing 230, so that forces from the surfaces of the holes 280 engaging the fragment attachment pins 218 in opposite directions hold these pins 218 in place.

Preferably, a clamp retaining means 304 is additionally provided to hold the pin clamping bracket 286 in place on the housing 230 in the absence of any fragment attachment pins 218. For example, the clamp retaining means 304 includes a pin 306 extending from the housing 230 within a hole 308 in each of the plates 284, 288 of the pin clamping bracket 286, with the hole 308 being large enough to allow the movement of the plates 284, 288 as described above A ramp surface 310 is provided at an edge of each of the plates 284, 288 so that the pin clamping bracket 286 can be snapped in place over the pins 306.

The angularly adjustable fragment mounting pins 220 are each attached rotatably mounted and clamped in place as described above in reference to FIGS. 2-4, with various similar elements being accorded like reference numbers.

In the treatment of a particular facture, fragment mounting pins 218, 220 will be placed in only some of the positions provided for such pins within the device 200. A larger number of such positions are provided, and the angular adjustability of the fragment mounting pins 220 is further provided, so that the device 200 can be used to treat a wide number of different fracture conditions.

Figure 15:
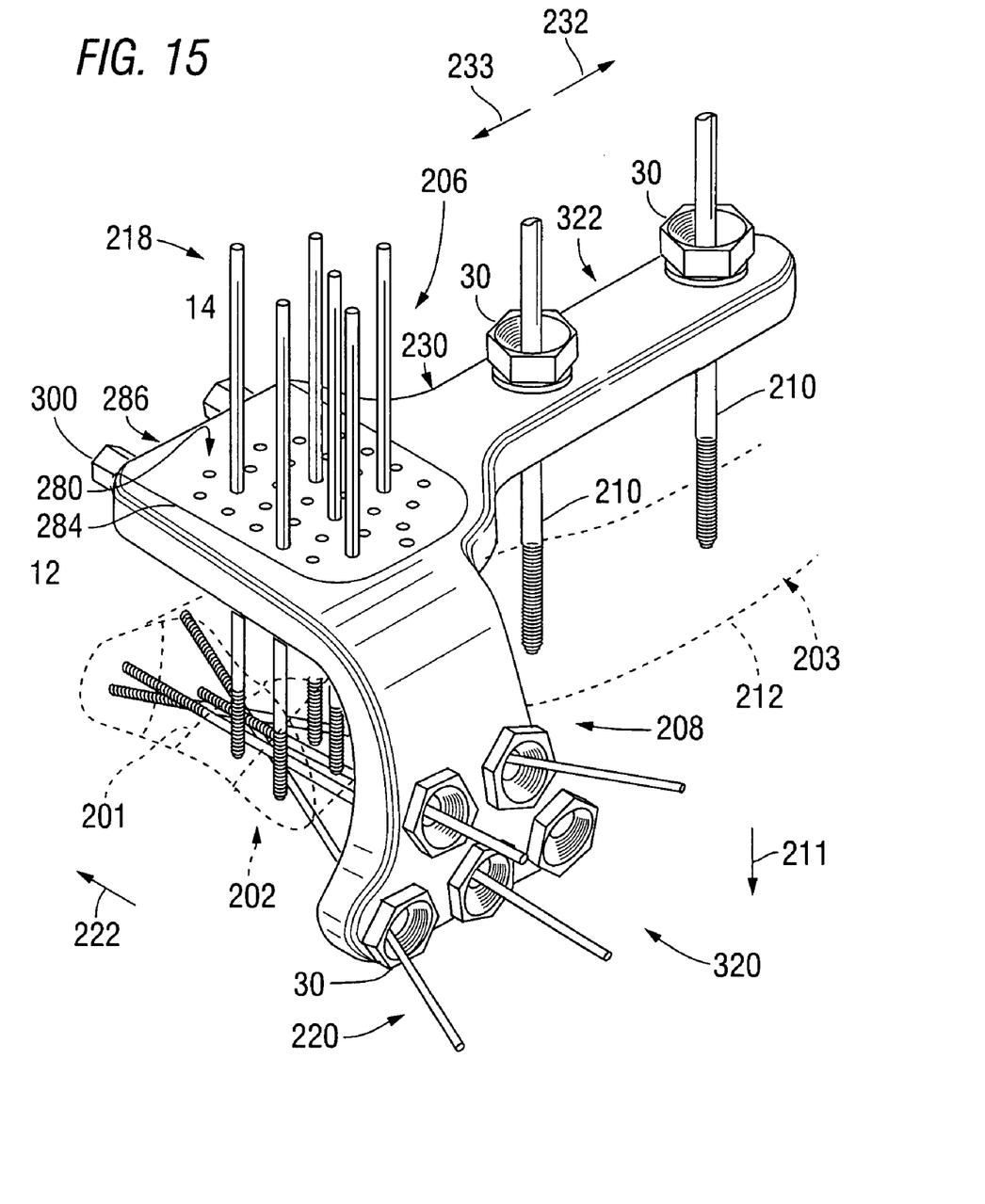
FIG. 15 is a perspective view of a device built in accordance with an alternative version of the third embodiment of the invention for the external fixation of fragments within a fractured distal radius.

FIG. 15 is a perspective view of a device 320 built in accordance with an alternative version of the third embodiment of the invention to have an elongated shank mounting section 322 having two angularly adjustable shank mounting pins 210 instead of one angularly adjustable shank mounting pin 210 and a linearly adjustable shank mounting pin 216. Other aspects of the device 320 are as described above in reference to FIGS. 11-14.

While versions of the devices 200, 320 adapted for providing fixation for a fractured distal radius of the right arm has been shown and described, it is understood that a similar device, having a housing that is a mirror image of the housing 230 described herein, may be configured for providing fixation for a fractured distal radius of the left arm, and that such a device is within the spirit and scope of the invention. It is further understood that apparatus in accordance with the third embodiment of this invention may be readily employed to provide fixation for bone fragments at an end of another bone. While the invention has been described in terms of its preferred embodiments with some degree of particularity, it is understood that this description has been given only by way of example, and that many variations can be made without departing from the spirit and scope of the invention, as defined in the appended claims.

What is claimed is:

1. Apparatus for external fixation of a plurality of fragments at an end of a bone, wherein the apparatus comprises:
   a housing including an elongated shank mounting portion, a fragment attachment pin array section at a first end of the elongated shank mounting portion having a first array of pin mounting holes, and a lateral fragment mounting section extending parallel to the elongated shank mounting portion and downward from an edge of the fragment attachment pin array section; wherein the lateral fragment mounting section includes a first plurality of apertures, an internal mounting surface adjacent each of the apertures, and a threaded surface adjacent each of the apertures;
   a first plurality of bone pins, clamped within the shank mounting portion and extending downward from the shank mounting portion for attachment within a shank portion of the bone;
   a clamping bracket including a clamping plate having a second array of pin mounting holes;
   a second plurality of bone pins, extending through holes within the first array of pin mounting holes and through holes within the second array of pin mounting holes, and extending downward for attachment to fragments within the plurality of fragments;
   at least one clamping screw holding the clamping bracket against the housing so that the second array of holes is misaligned with the first array of holes to hold the second plurality of bone pins in place within the first array of holes;
   a third plurality of bone pins, clamped within the lateral fragment mounting section and extending laterally for attachment to fragments within the plurality of fragments;
   a first plurality of pin holders held within the housing, wherein each of the pin holders includes a spherical external surface held within the internal mounting surface adjacent an aperture in the first plurality of apertures, a pin mounting hole extending in a straight line through a center of the spherical external surface, and a pair of slots extending across the pin mounting hole and partially across the pin holder, wherein each of the slots is displaced inward from one of the ends of the pin mounting hole to form a deflectable portion of the pin holder, extending between the slot and the end of the pin mounting hole, with a deflectable part of the pin mounting hole extending through each deflectable portion of the pin holder, and with a central part of the pin mounting hole extending through a central portion of the pin holder;
   the third plurality of bone pins each held within the pin mounting hole in a pin holder within the first plurality of pin holders to extend through an aperture in the first plurality of apertures, wherein an angle, relative to the housing, at which each of the bone pins extends through the aperture is varied by pivoting the pin holder within the housing; and
   a plurality of clamping members, wherein each of the clamping members includes a threaded portion engaging the threaded surface adjacent one of the apertures within the housing and a surface engaging one of the deflectable portions of a pin holder within the plurality of pin holders, wherein, as each of the clamping members is rotated in a first direction, an engagement force between the spherically rounded external surface of the pin holder and the internal mounting surface in which the pin holder is held is increased to hold the pin holder in place within the internal mounting surface, while misalignment between the deflectable parts and the central part of the pin mounting hole is increased to hold the bone pin in place within the pin mounting hole, and wherein as each of the clamping members is rotated opposite the first direction, the engagement force between the spherically rounded external surface of the pin holder and the internal mounting surface in which the pin holder is held is decreased to allow movement of the pin holder within the internal mounting surface, while misalignment between the deflectable parts and the central part of the pin mounting hole is decreased to release the bone pin to move within the pin mounting hole.

2. The apparatus of claim 1, wherein the pair of slots extend in directions perpendicular to the pin mounting hole.

3. The apparatus of claim 1, additionally comprising:
   within the elongated shank mounting portion, an additional aperture, an additional internal mounting surface adjacent the additional aperture, and an additional threaded surface adjacent the additional aperture;
   an additional pin holder including a spherical external surface held within the additional internal mounting surface, a pin mounting hole extending in a straight line through a center of the spherical external surface, and a pair of slots extending across the pin mounting hole and partially across the pin holder, wherein each of the slots is displaced inward from one of the ends of the pin mounting hole to form a deflectable portion of the pin holder, extending between the slot and the pin mounting hole, with a deflectable part of the pin mounting hole extending through each deflectable portion of the pin holder, and with a central part of the pin mounting hole extending through a central portion of the pin holder;

a bone pin within the first plurality of bone pins held within the pin mounting hole of the additional pin holder to extend through the aperture;

a clamping member, including a threaded portion engaging the threaded surface of the housing and a surface engaging one of the deflectable portions of the additional pin holder, wherein, as the clamping member is rotated in a first direction, an engagement force between the spherically rounded external surface of the additional pin holder and the internal mounting surface is increased to hold the additional pin holder in place within the additional internal mounting surface, while misalignment between the deflectable parts and the central part of the pin mounting hole is increased to hold the bone pin in place within the pin mounting hole, and wherein as the clamping member is rotated opposite the first direction, the engagement force between the spherically rounded external surface of the additional pin holder and the internal mounting surface is decreased to allow movement the additional pin holder within the internal mounting surface, while misalignment between the deflectable parts and the central part of the pin mounting hole is decreased to release the bone pin to move within the additional pin holder.

4. The apparatus of claim 3, wherein the pair of slots extend in directions perpendicular to the pin mounting hole within the additional pin holder.

5. The apparatus of claim 1, wherein the clamping bracket additionally includes a hole engaging a pin extending from the housing to hold the clamping bracket in place on the housing without a bone pin extending through a hole within the first and second arrays of pin mounting holes.

6. The apparatus of claim 1, wherein
the clamping bracket additionally comprises an additional clamping plate having a third array of pin mounting holes, and
the second and third arrays of mounting holes are held adjacent opposite sides of the first array of pin mounting holes.

7. The apparatus of claim 1, wherein the elongated shank mounting portion additionally includes a pin adjustment slot, additionally comprising:
a nut slidably mounted within the pin adjustment slot, including inclined surfaces engaging the pin adjustment slot to prevent rotation of the nut within the pin adjustment slot and to prevent removal of the nut from the pin adjustment slot;
a collet screw additionally sliding within the pin adjustment slot, wherein a linearly adjustable bone pin within the first plurality of bone pins extends through a hole within the collet screw, wherein the collet screw includes a deformable threaded portion engaging the nut, wherein, as the collet screw is rotated in a first direction, an engagement force between the collet screw and the linearly adjustable bone pin is increased to hold the linearly adjustable bone pin in place and to hold the nut in place within the pin adjustment slot, and
wherein, as the collet screw is rotated opposite the first direction, the engagement force between the collet screw and the linearly adjustable bone pin is decreased to release the linearly adjustable bone pin to move within the collet screw and the nut is released to slide within the pin adjustment slot.

8. The apparatus of claim 7, additionally comprising:
a distraction clamp removably holding the linearly adjustable bone pin; and
a distraction screw engaging the distraction clamp and the housing, wherein turning the distraction screw in a second direction moves the linearly adjustable bone pin toward a proximal end of the housing, and wherein turning the distraction screw opposite the second direction allows the linearly adjustable bone pin to move away from the proximal end of the housing.

9. The apparatus of claim 1, additionally comprising:
within the elongated shank mounting portion, a second plurality of apertures, an internal mounting surface adjacent each of the apertures, and a threaded surface adjacent each of the apertures;
a second plurality of pin holders held within the housing, wherein each of the pin holders includes a spherical external surface held within the internal mounting surface adjacent an aperture in the second plurality of apertures, a pin mounting hole extending in a straight line through a center of the spherical external surface, and a pair of slots extending across the pin mounting hole and partially across the pin holder, wherein each of the slots is displaced inward from one of the ends of the pin mounting hole to form a deflectable portion of the pin holder, extending between the slot and the end of end of the pin mounting hole, with a deflectable part of the pin mounting hole extending through each deflectable portion of the pin holder, and with a central part of the pin mounting hole extending through a central portion of the pin holder;
the first plurality of bone pins, each held within the pin mounting hole in a pin holder within the second plurality of pin holders to extend through an aperture in the second plurality of apertures, wherein an angle, relative to the housing, at which each of the bone pins extends through the aperture is varied by pivoting the pin holder within the housing, and
a second plurality of clamping members, wherein each of the clamping members includes a threaded portion engaging the threaded surface adjacent an aperture in the second plurality of apertures within the housing and a surface engaging the deflectable portion of a pin holder within the second plurality of pin holders, wherein, as each of the clamping members is rotated in a first direction, an engagement force between the spherically rounded external surface of the pin holder and the internal mounting surface in which the pin holder is held is increased to hold the pin holder in place within the internal mounting surface, while misalignment between the deflectable parts and the central part of the pin mounting hole is increased to hold the bone pin in place within the pin mounting hole, and wherein as each of the clamping members is rotated opposite the first direction, the engagement force between the spherically rounded external surface of the pin holder and the internal mounting surface in which the pin holder is held is decreased to allow movement the pin holder within the internal mounting surface, while misalignment between the deflectable parts and the central part of the pin mounting hole is decreased to release the bone pin to move within the pin mounting hole.

10. The apparatus of claim 9, wherein the pair of slots extend in directions perpendicular to the pin mounting hole.

11. The apparatus of claim 9, wherein the pair of slots extend in directions perpendicular to the pin mounting hole.

12. Apparatus for external fixation of a plurality of fragments at an end of a bone, wherein the apparatus comprises:
a housing including an elongated shank mounting portion and a fragment attachment pin array section at a first end of the elongated shank mounting portion having a first array of pin mounting holes;

a first plurality of bone pins, clamped within the shank mounting portion and extending downward from the shank mounting portion for attachment within a shank portion of the bone;

a clamping bracket including a clamping plate having a second array of pin mounting holes and a hole engaging a pin extending from the housing to hold the clamping bracket in place on the housing without a bone pin extending through a hole within the first and second arrays of pin mounting holes;

a second plurality of bone pins, extending through holes within the first array of pin mounting holes and through holes within the second array of pin mounting holes, and extending downward for attachment to fragments within the plurality of fragments;

at least one clamping screw holding the clamping bracket against the housing so that the second array of holes is misaligned with the first array of holes to hold the second plurality of bone pins in place within the first array of holes;

the elongated shank mounting portion including a plurality of apertures, an internal mounting surface adjacent each of the apertures, and a threaded surface adjacent each of the apertures;

a plurality of pin holders held within the housing, wherein each of the pin holders includes a spherical external surface held within the internal mounting surface adjacent an aperture in the plurality of apertures, a pin mounting hole extending in a straight line through a center of the spherical external surface, and a pair of slots extending across the pin mounting hole and partially across the pin holder, wherein each of the slots is displaced inward from one of the ends of the pin mounting hole to form a deflectable portion of the pin holder, extending between the slot and the end of end of the pin mounting hole, with a deflectable part of the pin mounting hole extending through each deflectable portion of the pin holder, and with a central part of the pin mounting hole extending through a central portion of the pin holder;

the first plurality of bone pins each held within the pin mounting hole in a pin holder within the plurality of pin holders to extend through an aperture in the plurality of apertures, wherein, an angle, relative to the housing, at which each of the bone pins extends through the aperture is varied by pivoting the pin holder within the housing, and a plurality of clamping members, wherein each of the clamping members includes a threaded portion engaging the threaded surface adjacent one of the apertures within the housing and a surface engaging the deflectable portion of a pin holder within the plurality of pin holders, wherein, as each of the clamping members is rotated in a first direction, an engagement force between the spherically rounded external surface of the pin holder and the internal mounting surface in which the pin holder is held is increased to hold the pin holder in place within the internal mounting surface, while misalignment between the deflectable parts and the central part of the pin mounting hole is increased to hold the bone pin in place within the pin mounting hole, and wherein as each of the clamping members is rotated opposite the first direction, the engagement force between the spherically rounded external surface of the pin holder and the internal mounting surface in which the pin holder is held is decreased to allow movement of the pin holder within the internal mounting surface, while misalignment between the deflectable parts and the central part of the pin mounting hole is decreased to release the bone pin to move within the pin mounting hole.

13. The apparatus of claim 12, wherein the clamping bracket additionally comprises an additional clamping plate having a third array of pin mounting holes, and the second and third arrays of mounting holes are held adjacent opposite sides of the first array off pin mounting holes.

* * * * *